United States Patent
Thinon et al.

(10) Patent No.: US 12,157,792 B2
(45) Date of Patent: Dec. 3, 2024

(54) METHOD FOR PRODUCING A POLYESTER TEREPHTHALATE INCORPORATING A DEPOLYMERIZATION METHOD

(71) Applicant: IFP Energies nouvelles, Rueil-Malmaison (FR)

(72) Inventors: Olivier Thinon, Rueil-Malmaison (FR); Thierry Gauthier, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 699 days.

(21) Appl. No.: 17/427,450

(22) PCT Filed: Jan. 27, 2020

(86) PCT No.: PCT/EP2020/051844
§ 371 (c)(1),
(2) Date: Jul. 30, 2021

(87) PCT Pub. No.: WO2020/156965
PCT Pub. Date: Aug. 6, 2020

(65) Prior Publication Data
US 2022/0127416 A1 Apr. 28, 2022

(30) Foreign Application Priority Data
Feb. 1, 2019 (FR) ...................... 1901024

(51) Int. Cl.
*C08G 63/78* (2006.01)
*C08G 63/183* (2006.01)
*C08J 11/24* (2006.01)
*C08L 67/02* (2006.01)

(52) U.S. Cl.
CPC .......... *C08G 63/183* (2013.01); *C08G 63/78* (2013.01); *C08J 11/24* (2013.01); *C08L 67/02* (2013.01); *C08J 2367/02* (2013.01); *C08L 2207/20* (2013.01)

(58) Field of Classification Search
USPC ....................................... 521/48.5
See application file for complete search history.

(56) References Cited

U.S. PATENT DOCUMENTS

| | | |
|---|---|---|
| 4,001,187 A | 1/1977 | Itabashi et al. |
| 4,578,502 A | 3/1986 | Cudmore |
| 5,502,247 A | 3/1996 | Bartos et al. |
| 5,504,121 A | 4/1996 | West |
| 5,869,543 A | 2/1999 | Boos et al. |
| 6,642,350 B1 | 11/2003 | Asakawa et al. |
| 7,030,264 B1 | 4/2006 | Inada et al. |
| 7,193,104 B2 | 3/2007 | Inada et al. |
| 10,544,276 B2 | 1/2020 | Charra et al. |
| 2004/0147624 A1 | 7/2004 | Inada et al. |
| 2004/0182782 A1 | 9/2004 | Inada et al. |
| 2006/0074136 A1 | 4/2006 | Smith et al. |
| 2015/0105532 A1 | 4/2015 | Allen et al. |
| 2019/0161595 A1 | 5/2019 | Charra et al. |

FOREIGN PATENT DOCUMENTS

| | | |
|---|---|---|
| EP | 0723951 A1 | 7/1996 |
| EP | 1306364 A1 | 5/2003 |
| EP | 1120394 B1 | 9/2004 |
| EP | 1234812 B1 | 5/2008 |
| FR | 2046924 A7 | 3/1971 |
| FR | 3053691 A1 | 1/2018 |
| GB | 776282 A | 6/1957 |
| GB | 931314 A | 7/1963 |
| JP | 2003306603 A | 10/2003 |
| WO | 16096768 A1 | 6/2016 |
| WO | 17006217 A1 | 1/2017 |
| WO | 18007356 A1 | 1/2018 |

OTHER PUBLICATIONS

International Search Report PCT/EP2020/051844 dated Mar. 10, 2020 (pp. 1-4).

*Primary Examiner* — Terressa Boykin
(74) *Attorney, Agent, or Firm* — Millen White Zelano & Branigan; Csaba Henter

(57) ABSTRACT

The invention relates to a process for producing a terephthalate polyester from at least one feedstock of polyester to be recycled, integrating a process of depolymerization, advantageously by glycolysis, of the polyester to be recycled in order to produce a diester intermediate compatible with the specifications of the polymerization steps and comprising an optimized system for recycling the streams.

13 Claims, 1 Drawing Sheet

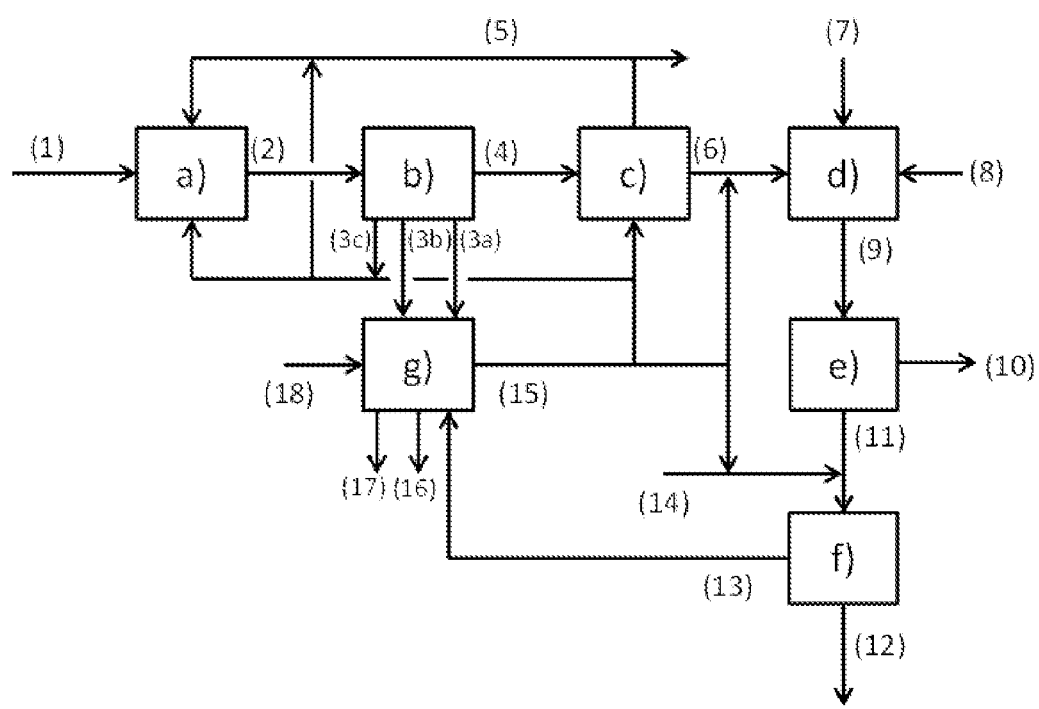

METHOD FOR PRODUCING A POLYESTER TEREPHTHALATE INCORPORATING A DEPOLYMERIZATION METHOD

TECHNICAL FIELD

The invention relates to a process for producing a polyester, in particular a polyethylene terephthalate (PET), integrating a process of depolymerization of a feedstock of polyester to be recycled, in particular comprising an opaque polyester.

PRIOR ART

The chemical recycling of polyester, in particular of polyethylene terephthalate (PET) has been the subject of numerous studies targeted at breaking down the polyester recovered in the form of waste into monomers which will again be able to be used as feedstock for a polymerization process.

Numerous polyesters result from circuits for collecting and sorting materials. In particular, polyester, especially PET, can originate from the collection of bottles, containers, films, resins and/or fibres composed of polyester (such as, for example, textile fibres, tyre fibres). The polyester resulting from collecting and sorting industries is known as polyester to be recycled. PET to be recycled can be classified into four main categories:

- clear PET, predominately composed of colourless transparent PET (generally at least 60% by weight) and azure coloured transparent PET, which does not contain pigments and can be used in mechanical recycling processes;
- dark or coloured (green, red, and the like) PET, which can generally contain up to 0.1% by weight of dyes or pigments but remains transparent or translucent;
- opaque PET, which contains a significant amount of pigments at contents typically varying between 0.25% and 5.0% by weight in order to opacify the polymer. Opaque PET is increasingly being used, for example in the manufacture of food containers, such as milk bottles, in the composition of cosmetic, plant-protection or dye bottles;
- multilayer PET, which comprises layers of polymers other than PET or a layer of recycled PET between layers of virgin PET (that is to say, PET which has not undergone recycling), or a film of aluminium, for example. Multilayer PET is used, after thermoforming, to produce packagings, such as containers.

The collecting industries which make it possible to supply the recycling industries are structured differently depending on the country. They are changing so as to maximize the amount of plastic recycled from waste as a function of the nature and of the amount of the streams and of the sorting technologies. The industry for recycling these streams generally consists of a first step of conditioning in the form of flakes during which bales of raw packaging are washed, purified and sorted, ground and then again purified and sorted to produce a stream of flakes generally containing less than 1% by weight of "macroscopic" impurities (glass, metals, other plastics, wood, paper, cardboard, inorganic elements), preferentially less than 0.2% of "macroscopic" impurities and more preferentially still less than 0.05%.

Clear PET flakes can subsequently undergo a step of extrusion-filtration which makes it possible to produce extrudates which can subsequently be reused as a mixture with virgin PET to produce new products (bottles, fibres, films). A step of solid state polymerization under vacuum (known under the acronym SSP) is necessary for food uses. This type of recycling is known as mechanical recycling.

Dark (or coloured) PET flakes can also be recycled mechanically. However, the colouration of the extrudates formed from the coloured streams limits the uses: dark PET is generally used to produce packaging straps or fibres. The outlets are thus more limited in comparison with those of clear PET.

The presence of opaque PET containing pigments at high contents, in PET to be recycled, presents problems to recyclers as opaque PET detrimentally affects the mechanical properties of recycled PET. Opaque PET is currently collected with coloured PET and is found in the coloured PET stream. In view of the development of the uses for opaque PET, the contents of opaque PET in the stream of coloured PET to be recycled are currently between 5-20% by weight and are tending to increase further. In a few years time, it will be possible to achieve contents of opaque PET in the coloured PET stream of greater than 20-30% by weight. In point of fact, it has been shown that, above 10-15% of opaque PET in the coloured PET streams, the mechanical properties of the recycled PET are detrimentally affected (cf. Impact du développement du PET opaque blanc sur le recyclage des emballages en PET [Impact of the growth of white opaque PET on the recycling of PET packagings], preliminary report of COTREP of May 12, 2013) and prevent recycling in the form of fibres, the main outlet of the industry for coloured PET.

Dyes are natural or synthetic substances which are soluble, in particular in the polyester material, and are used to colour the material into which they are introduced. The dyes generally used have different natures and often contain heteroatoms of O and N type, and conjugated unsaturations, such as, for example, quinone, methine or azo functions, or molecules such as pyrazolone and quinophthalone. Pigments are finely divided substances which are insoluble, in particular in the polyester material, and which are used to colour and/or opacify the material into which they are introduced. The main pigments used to colour and/or opacify the polyesters, in particular PET, are metal oxides, such as $TiO_2$, $CoAl_2O_4$ or $Fe_2O_3$, silicates, polysulfides and carbon black. The pigments are particles with a size generally of between 0.1 and 10 µm and predominantly between 0.4 and 0.8 µm. The complete removal of these pigments by filtration, which is necessary in order to envisage recycling the opaque PET, is technically difficult as they have an extremely high clogging capability.

The recycling of coloured and opaque PETs is thus extremely problematic.

Several processes for chemical recycling of polyester, in particular of PET have been proposed in the literature but are not all intended for the same final product, which product is then used to again manufacture a terephthalate ester polymer.

In particular, patent application MX 2007/004429 discloses the production of a polyester of good quality, comprising a process for the depolymerization by glycolysis at atmospheric pressure of PET flakes in the presence of ethylene glycol in a bis(2-hydroxyethyl) terephthalate (BHET) base. The intermediate product obtained at the end of the depolymerization step is filtered through a sintered system in order to retain particles of at least 25 µm before being introduced into the polymerization reactor, in order to obtain a polyester of good quality. In U.S. Pat. No. 4,578, 502, monomers of carboxylic acid in crystalline form and a polyol in liquid form are recovered after depolymerization of a polyalkylene terephthalate resin by hydrolysis or methanolysis, then recombined to reform polyester. Patent application WO 2013/025186 itself describes a process for preparing a copolyester having a high recycled monomer content, comprising a step of depolymerization by methanolysis, a step of separation of the dimethyl terephthalate released then the polymerization of the dimethyl terephthalate with at least one polyol.

Patent application US 2006/0074136 describes a process for the depolymerization by glycolysis of coloured PET, in particular resulting from the recovery of green-coloured PET bottles. The BHET stream obtained at the end of the glycolysis step is purified through active carbon in order to separate certain dyes, such as blue dyes, and then by extraction of the residual dyes, such as yellow dyes, by an alcohol or by water. The BHET, which crystallizes from the extraction solvent, is then separated, for the purpose of being able to be used in a PET polymerization process. In patent application US 2015/0105532, post-consumer PET, comprising a mixture of various coloured PETs, such as clear PET, blue PET, green PET and/or amber PET, is depolymerized by glycolysis in the presence of an amine catalyst and of alcohol. The diester monomer then obtained can be purified by filtration, ion exchange and/or by passing through active carbon, before being crystallized and recovered by filtration in order to be polymerized and to thus reform a polyester.

Patent application WO 2017/006217 discloses the process for the preparation of a polyethylene terephthalate glycol-modified (r-PETG) comprising a step of depolymerization of a PET in the presence of a mixture of monoethylene glycol (MEG) and of neopentyl glycol, followed directly by a step of polymerization of the reaction effluent.

Patent application FR 3053691 describes a process for the depolymerization of a polyester feedstock comprising in particular from 0.1% to 10% by weight of pigments, by glycolysis in the presence of ethylene glycol. An effluent of bis(2-hydroxyethyl) terephthalate (BHET) monomers, which is obtained after specific separation and purification steps, can supply a polymerization step for the purpose of producing PET, without any condition being specified.

In patent EP0865464, the process for depolymerization of polyesters, the nature of which is not specified, comprises the steps of depolymerization in the presence of a diol, of evaporation of the diol, of dissolution of the mixture in a hot solvent, of filtration and of precipitation of the filtered solution, it being possible for the precipitate to be subsequently used in the preparation of a new polymer.

Patent JP3715812 describes the production of refined BHET from PET, it being possible for the BHET obtained to be used as raw material in a process for the production of plastic products. The depolymerization is followed by a step of prepurification by cooling, filtration, adsorption and treatment on an ion-exchange resin which is presented as very important, carried out before the evaporation of the glycol and the purification of the BHET. The prepurification makes it possible to prevent the re-polymerization of the BHET in the subsequent purification steps. However, passing through a step of filtration and ion-exchange resin can be extremely problematic when the feedstock comprises a large amount of very small solid particles, such as pigments, which is the case when the feedstock treated comprises opaque PET, in particular in sizeable proportions (more than 10% by weight of opaque PET). In the same way, patent EP 1 120 394 discloses the optional use, as raw material for reproducing a high-quality polyester, of high-purity bis(2-hydroxyethyl) terephthalate. For this, patent EP 1 120 394 describes a process for depolymerization of a polyester comprising a step of glycolysis in the presence of ethylene glycol and a process for purification of a solution of bis(2-hydroxyethyl) terephthalate on a cation-exchange resin and an anion-exchange resin.

None of these documents proposes the direct linking of the steps of depolymerization, in particular of PET to be recycled comprising dark and/or opaque PET, and of polymerization of the intermediate products obtained, with an optimized integration notably of the material streams, in particular of the diol streams, enabling a sizeable reduction in the consumption of raw materials and of energy.

SUMMARY OF THE INVENTION

The subject of the invention is a process for producing a terephthalate polyester from at least one feedstock of polyester to be recycled, comprising at least the following steps:

a) a step of depolymerization of said feedstock of polyester to be recycled, comprising at least one reaction section fed with said feedstock of polyester to be recycled and with a glycol feedstock, wherein said reaction section is operated, at a temperature between 150° C. and 400° C., preferably between 180° C. and 300° C., preferably between 200° C. and 280° C., at a pressure of at least 0.1 MPa, preferentially at least 0.4 MPa, and with a residence time per reactor of between 0.05 and 10 h, in order to obtain a depolymerization reaction effluent, b) a separation step, comprising at least one separation section fed with said depolymerization reaction effluent obtained at the end of the depolymerization step a), in order to obtain at least one glycol effluent and one diester effluent, c) a step for purifying the diester effluent obtained at the end of step b), comprising at least one separation section that is fed with said diester effluent obtained at the end of step b) and operated at a temperature below or equal to 250° C., at a pressure less than or equal to 0.001 MPa, and with a liquid residence time per section of the less than equal to 10 min, then a discolouration section operated at a temperature between 100° C. and 250° C. and at a pressure of between 0.1 and 1.0 MPa, in the presence of an adsorbent, in order to obtain a liquid purified diester effluent, d) a step for preparing a polymerization feedstock comprising at least one mixing section fed with at least one terephthalic feedstock, and at least one fraction of said purified diester effluent obtained in step c) in liquid form, wherein the amounts of at least said terephthalic feedstock and said fraction of the purified diester effluent, introduced into said mixing section, is adjusted so that the ratio of the total number of moles of diol units of formula —[$C_{(n+1)}H_{(2n+2)}O_2$]—, n being an integer greater than or equal to 1, introduced into said mixing section, relative to the total number of moles of terephthalate units of formula —[CO—($C_6H_4$)—CO]—, introduced into said mixing section, is between 1.0 and 2.0, wherein said mixing section is operated at a temperature between 25° C. and 250° C. and at a pressure greater than or equal to 0.1 MPa, e) a step for condensing said polymerization feedstock resulting from step d), in order to produce at least one condensation reaction effluent, one diol effluent and one aqueous effluent or one methanol effluent, wherein said condensation step comprises at least one reaction section operated at a temperature between 150° C. and 400° C., at a pressure between 0.05 and 1 MPa, and with a residence time of between 1 and 10 h, and at least one separation section, f) a step of polycondensation of said condensation reaction effluent obtained in step e) in order to obtain at least said terephthalate polyester and a diol effluent, wherein said polycondensation step comprises at least one reaction section that comprises at least one reactor in which the polycondensation is carried out and that is operated at a temperature between 200° C. and 400° C., at a pressure between 0.0001 and 0.1 MPa, with a residence time between 0.1 and 5 h, said reaction section also comprising at least one drawing-off of said diol effluent, g) a step for treating the diols, comprising a recovery section fed at least by all or part of the glycol effluent resulting from step b) and all or part of the diol effluent resulting from step f), in order to obtain a diol stream to be treated, and a section for purification of said diol stream to be treated in order to obtain a purified diol stream.

Preferably, the present invention relates to a process for producing a terephthalate polyester from at least one feedstock of polyester to be recycled consisting of the steps a), b), c), d), e), f) and g), described above.

A major advantage of the present invention lies in the production of a polyester from, at least in part, a compound derived from polyester to be recycled, the polyester to be recycled notably comprising opaque polyester, in a sizeable amount and which is in accordance with the amount encountered in the polyester material resulting from collecting and sorting industries, without deterioration of the quality of the polyester produced. Specifically, the present invention enables the production of a polyester from, at least in part, polyester to be recycled which has properties, in particular physicochemical and mechanical properties, similar to those of a virgin polyester of the same type.

The present invention, which relates to a specific process comprising a linking of a process for depolymerization, in particular by glycolysis, of a polyester material to be recycled and of a process for polymerization of a polyester, enables an integration of streams of materials. It enables more particularly, notably by a specific recycling system, an optimized integration of the diol streams introduced and recovered between the depolymerization and polymerization phases. The present invention also enables the production of a liquid purified diester intermediate which corresponds to the specifications of the polymerization process and which can therefore directly supply the steps of polymerization without an intermediate step of purification and/or of conditioning, such as for example the crystallization of said intermediate then the transition of said crystalline diester intermediate to a liquid phase, which makes it possible to avoid additional handling operations and a high energy consumption. At the same time, the incorporation of a purified diester intermediate obtained in liquid form at the end of the depolymerization steps, into the polymerization steps, in particular into the mixture of monomers, makes it possible to reduce the amount of the diol monomer feedstock supplying the polymerization process, while retaining a good operability notably of the step of preparing the mixture of monomers of the polymerization process. Since the amount of diol introduced into the mixture is reduced, the amount of diol to be recycled in the subsequent operations of the polymerization process is decreased, thus reducing the energy consumption of the overall process for producing a polyester from, at least in part, polyester material to be recycled.

Another advantage of the present invention is sharing of operations for recovering and purifying diol effluents resulting from the depolymerization process and from the polymerization process, specifically leading to a reduction in the energy consumptions of the overall process and reduced equipment costs.

DESCRIPTION OF THE EMBODIMENTS

The invention relates to a process for producing a polyester, that integrates a process of depolymerization of a feedstock of polyester to be recycled, in particular comprising an opaque polyester.

According to the invention, the terms "polyester", "terephthalate polyester" and "polyalkylene terephthalate" are interchangeable and denote a polymer (i.e. a molecule of high molecular mass consisting of monomers combined with one another by covalent bonds) the basic repeating unit of which comprises a terephthalate unit —[CO—($C_6H_4$)—O]—, where —($C_6H_4$)— represents an aromatic ring, covalently bonded to a diol unit —[O—$C_{(n+1)}H_{(2n+2)}$—O]—, where n is an integer greater than or equal to 1, preferably between 1 and 5, preferentially between 1 and 3. Very conventionally, a polyalkylene terephthalate is the result of the polycondensation of a diol (or glycol) monomer with a terephthalic acid (or dimethyl terephthalate) monomer. The terephthalate polyester, or polyalkylene terephthalate, according to the invention is, in particular, polyethylene terephthalate (PET), polybutylene terephthalate (PBT), polytrimethylene terephthalate (PTT) or any other polymer, the repeating unit of the main chain of which contains an ester function and an aromatic ring derived from terephthalic acid (or from one of its esters, in particular dimethyl terephthalate). According to the invention, the preferred terephthalate polyester is polyethylene terephthalate or poly(ethylene terephthalate), also known simply as PET, the basic repeating unit of which has the following formula:

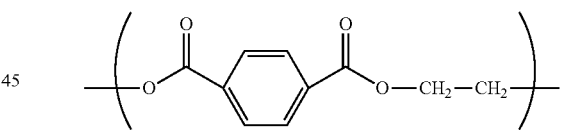

Conventionally, PET is obtained by polycondensation of terephthalic acid (PTA) or dimethyl terephthalate (DMT) with ethylene glycol.

According to the invention, the expression "to be recycled" describes any material, in particular comprising polyester, resulting from industries for collecting and sorting plastic waste. In contrast, a virgin polyester results solely from the polymerization of monomer feedstocks comprising at least one dicarboxylic acid (for example terephthalic acid, PTA) or one dicarboxylic ester (for example dimethyl terephthalate, DMT) and at least one compound from the family of diols or glycols (for example ethylene glycol).

According to the invention, the term "diester monomer" denotes a terephthalate ester compound of chemical formula $HOC_{(m+1)}H_{(2m+2)}$—$CO_2$—($C_6H_4$)—$CO_2$—$C_{(n+1)}H_{(2n+2)}$OH, in which: —($C_6H_4$)— represents an aromatic ring; n and m are integers which are identical or different, preferably identical (that is to say, n=m), and greater than or equal to 1, preferably between 1 and 5, preferably between 1 and 3. A molecule of diester monomer corresponds to a compound which would result from the esterification of one molecule of terephthalic acid HOOC—$(C_6H_4)$—COOH (where —$(C_6H_4)$— represents an aromatic ring) with two molecules of at least one diol (or glycol), more particularly with one molecule of a diol of chemical formula HO—$C_{(n+1)}H_{(2n+2)}$—OH and one molecule of a diol of chemical formula HO—$C_{(m+1)}H_{(2m+2)}$—OH. The preferred diester monomer is bis(2-hydroxyethyl) terephthalate (BHET).

The term oligomer typically denotes a polymer of small size, generally consisting of 2 to 20 basic repeating units.

According to the invention, the term "ester oligomer" denotes a terephthalate ester oligomer comprising between 2 and 20, preferably between 2 and 5, basic repeating units of formula —[O—CO—$(C_6H_4)$—CO—O—$C_{(n+1)}H_{(2n+2)}$]+, with: —$(C_6H_4)$— being an aromatic ring and n being an integer greater than or equal to 1, preferably between 1 and 5, preferably between 1 and 3.

The term "dye" is understood to mean a substance which is soluble in the polyester material and which is used to colour it. The dye can be of natural or synthetic origin.

The term "pigment", more particularly colouring and/or opacifying pigment, is understood to mean a finely divided substance which is insoluble in the polyester material. The pigments are in the form of particles with a size generally of between 0.1 and 10 µm and predominantly between 0.4 and 0.8 µm. They are often of inorganic nature. The pigments generally used, notably for opacifying, are metal oxides, such as $TiO_2$, $CoAl_2O_4$ or $Fe_2O_3$, silicates, polysulfides and carbon black.

According to the present invention, the expression "between . . . and . . . " means that the limiting values of the interval are included in the range of values which is described. If such were not the case and if the limiting values were not included in the range described, such an clarification will be given by the present invention.

Feedstocks

In accordance with the invention, said process is supplied with at least one feedstock of polyester to be recycled.

Advantageously, said feedstock of polyester to be recycled results from the industries for collecting and sorting waste, in particular plastic waste. Said feedstock of polyester to be recycled may originate, for example, from the collection of bottles, containers, films, resins and/or fibers constituted of polyethylene terephthalate.

Said feedstock of polyester to be recycled may be, completely or partly, in the form of flakes, the greatest length of which is less than 10 cm, preferentially between 5 and 25 mm, or in micronized solid form, that is to say in the form of particles preferably having a size of between 10 microns and 1 mm. The feedstock of polyester to be recycled preferably comprises less than 2% by weight, preferentially less than 1% by weight, of "macroscopic" impurities, such as glass, metal, plastic other than terephthalate polyester, wood, paper, cardboard or inorganic elements. Said feedstock of polyester to be recycled may also be, completely or partly, in the form of fibres, such as textile fibres, optionally pretreated in order to remove cotton or polyamide fibres or any other textile fibre other than polyester fibre, or such as tyre fibres, optionally pretreated in order to remove in particular polyamide fibres or rubber or polybutadiene residues. Said feedstock of polyester to be recycled may further comprise polyester derived from production scraps from processes for polymerizing and/or transforming the polyester material.

Advantageously, said feedstock of polyester to be recycled contains more than 50% by weight of polyalkylene terephthalate, preferably more than 70% by weight, preferably more than 90% by weight, of polyalkylene terephthalate.

Preferably said feedstock of polyester to be recycled is a feedstock of polyethylene terephthalate to be recycled (or feedstock of PET to be recycled) which comprises more than 50% by weight of polyethylene terephthalate (PET), preferably more than 70% by weight of polyethylene terephthalate (PET), preferably more than 90% by weight of polyethylene terephthalate (PET). Said feedstock of PET to be recycled advantageously comprises opaque PET, dark (or colored) PET, multilayer PET, clear (i.e. colourless transparent and/or azure coloured transparent) PET and mixtures thereof, preferably at least opaque PET. Preferably, it comprises at least 10% by weight of opaque PET, very preferably at least 15% by weight of opaque PET.

Said feedstock of polyester to be recycled may contain up to 10% by weight of pigments, in particular between 0.1% and 10% by weight of pigments, notably between 0.1% and 5% by weight of pigments, and/or up to 1% by weight of dyes, in particular between 0.05% and 1% by weight of dyes, notably between 0.05% and 0.2% by weight of dyes.

Said feedstock of polyester to be recycled may also contain elements used as polymerization catalyst and/or as stabilizing agents in polyester production processes, such as antimony, titanium or tin.

In accordance with the invention, the depolymerization step a) is further supplied with a glycol feedstock. Said glycol feedstock comprises at least one, preferably one, glycol (or diol) compound, of a type identical to or different from the diol corresponding to the diol unit of the basic polyalkylene terephthalate unit of the feedstock of polyester to be recycled. Advantageously, the weight content of said glycol compound in said glycol feedstock is greater than or equal to 80% by weight, preferentially greater than or equal to 90% by weight, preferably greater than or equal to 95% by weight, relative to the total weight of said glycol feedstock.

Preferably, the glycol feedstock of the process which supplies the depolymerization step a) comprises ethylene glycol, also known as monoethylene glycol (MEG), advantageously in a weight content of greater than or equal to 80% by weight, preferentially greater than or equal to 90% by weight, preferably greater than or equal to 95% by weight, relative to the total weight of said glycol feedstock. In this case the glycol feedstock is referred to as an ethylene glycol feedstock.

The ethylene glycol may advantageously be produced by hydrolysis of ethylene oxide or by selective hydrogenation of glycolaldehyde or depolymerization of polyesters or by any other process that makes it possible to obtain an ethylene glycol feedstock with the specifications required by the polymerization processes. The ethylene glycol may also be derived from fossil hydrocarbon sources or from biomass.

Said glycol feedstock which supplies the depolymerization step a) of the process according to the invention advantageously comprises, preferably consists of, at least one fraction of said purified diol stream obtained at the end of step g) of the process for the production of the terephthalate polyester according to the invention.

In accordance with the invention, said process is also supplied, in step d) of preparation of a polymerization feedstock, with at least one terephthalic feedstock. According to the invention, a terephthalic feedstock is a terephthalate acid feedstock, which comprises terephthalic acid as compound with a terephthalate unit, or a dimethyl terephthalate feedstock, which comprises dimethyl terephthalate as compound with a terephthalate unit.

Said terephthalic feedstock comprises terephthalic acid (PTA) or dimethyl terephthalate (DMT), in a weight content of greater than or equal to 95% by weight, preferentially greater than or equal to 98% by weight, preferably greater than or equal to 99% by weight, relative to the total weight of said terephthalic acid.

In one preferred embodiment, said feedstock is a terephthalic feedstock which comprises terephthalic acid (PTA). The terephthalic acid of the terephthalic acid feedstock can advantageously be produced by oxidation of para-xylene or by depolymerization of polyesters or by any other process which makes it possible to obtain a terephthalic acid feedstock with the specifications required by the polymerization processes. The terephthalic acid can result from fossil hydrocarbon sources or from biomass.

The terephthalic acid feedstock is advantageously in powder form, that is to say in the form of solid terephthalic acid particles. The terephthalic acid particles incorporated in the mixture of monomers preferably have a mean diameter preferably of between 1 and 1000 µm, in particular between 30 and 500 µm and notably between 80 and 200 µm. The mean diameter of the terephthalic acid particles is determined by any method of particle size analysis known to a person skilled in the art, such as, for example, by laser diffraction or by screening, preferably by screening through a column of suitable screens according to a technique known to a person skilled in the art.

Depolymerization Step a)

In accordance with the invention, the process for the production of a terephthalate polyester comprises a step a) of depolymerization of a feedstock of polyester to be recycled, in order to obtain a depolymerization reaction effluent. Said depolymerization step a) comprises at least one reaction section which is fed with said feedstock of polyester to be recycled and with a glycol feedstock.

Advantageously, the feeding of said glycol feedstock is adjusted so that the amount of the glycol compound contained in said glycol feedstock corresponds, at the inlet of said reaction section, to 1 to 20 mol, preferably 3 to 10 mol, of glycol compound per mole of basic repeating unit of the polyester contained in said feedstock of polyester to be recycled.

Advantageously, said glycol feedstock advantageously comprises, preferably consists of, at least one fraction of said purified diol stream obtained at the end of step g) of the process for the production of the terephthalate polyester according to the invention.

Advantageously, the depolymerization step a) employs, in particular in said reaction section, a reaction for the glycolysis of the polyalkylene terephthalate of said feedstock of polyester to be recycled, in the presence of the glycol compound(s) of said glycol feedstock.

Said reaction section of the depolymerization step a) is carried out, preferably in one or more reactors, at a temperature of between 150° C. and 400° C., preferably between 180° C. and 300° C., preferably between 200° C. and 280° C., at a pressure of at least 0.1 MPa, preferentially at least 0.4 MPa, and with a residence time per reactor of between 0.05 and 10 h, preferentially between 0.1 and 6 h and preferably between 0.5 and 4 h. The residence time, in a reactor of said reaction section of step a), is defined as the ratio of the volume of reaction liquid in a reactor of said reaction section to the volume flow rate of the stream which feeds said reactor of said reaction section.

Any type of reactor known to a person skilled in the art that makes it possible to carry out a depolymerization or transesterification reaction may be used in the reaction section of step a). Preferably, the reactor(s) in the reaction section of step a) is(are) stirred by a mechanical stirring system or/and by recirculation loop or/and by fluidization. Said reactor(s) may comprise a conical base that makes it possible to bleed off the impurities. Advantageously, said reaction section of step a) may comprise a (some) tubular reactor(s) or a combination of a (some) stirred reactor(s) and tubular reactor(s) in series or in parallel.

In one particular embodiment of the invention, the depolymerization step a) comprises at least one reaction section fed by a feedstock of PET to be recycled and by an ethylene glycol feedstock, so that the amount of ethylene glycol contained in said ethylene glycol feedstock corresponds to 1 to 20 mol, preferably 3 to 10 mol, of ethylene glycol of said ethylene glycol feedstock per mole of basic repeating unit, i.e. of terephthalate unit in said feedstock of PET to be recycled, said reaction section being operated, in one or more reactors, at a temperature between 150° C. and 400° C., preferably between 180° C. and 300° C., preferably between 200° C. and 280° C., at an operating pressure of at least 0.1 MPa, preferentially at least 0.4 MPa, and with a residence time per reactor of between 0.05 and 10 h, preferably between 0.1 and 6 h and preferably between 0.5 and 4 h, said residence time per reactor being defined as the ratio of the liquid volume of the reactor to the volume flow rate of the stream which feeds said reactor.

The depolymerization reaction of step a) of the process according to the invention may be carried out with or without addition of a catalyst. When the depolymerization reaction is carried out after addition of a catalyst, the latter can be homogeneous or heterogeneous and chosen from the esterification catalysts known to a person skilled in the art, such as complexes, oxides and salts of antimony, tin or titanium, alkoxides of metals from Groups (I) and (IV) of the Periodic Table of the Elements, organic peroxides or acidic/basic metal oxides. Preferably, the depolymerization reaction is carried out without addition of catalyst.

The depolymerization reaction can also advantageously be carried out in the presence of a solid adsorbing agent in the powder or shaped form, the role of which is to capture at least one portion of the impurities, in particular of the coloured impurities, thus relieving the strain on the purification phase of step b). Said solid adsorbing agent is in particular an activated carbon.

The depolymerization reaction effluent obtained at the end of the depolymerization step a) comprises a mixture of diester monomers (i.e. of compounds of chemical formula $HOC_{(m+1)}H_{(2m+2)}-CO_2-(C_6H_4)-CO_2-C_{(n+1)}H_{(2n+2)}OH$, in which: $-(C_6H_4)-$ represents an aromatic ring; n and m are integers, which are identical or different, preferably identical, and greater than or equal to 1, preferably between 1 and 5, preferably between 1 and 3, of oligomers comprising between 1 and 5, preferably between 1 and 3, basic units of formula $-[O-CO-(C_6H_4)-CO-O-C_{(n+1)}H_{(2n+2)}]-$, with n an integer of between 1 and 5, preferably between 1 and 5, of diol compounds, of impurities possibly present in said feedstock of polyester to be recycled and of compounds possibly produced at the end of side reactions, such as, for example, etherification or decomposition reactions. The diol compounds possibly within the depolymerization reaction effluent are advantageously diol monomers and comonomers incorporated in the composition of the feedstock of polyester to be recycled and released at the end of the depolymerization reaction and the unreacted ones resulting from the glycol stream feeding the depolymerization step a). Said depolymerization reaction effluent may also contain unconverted polyesters and other polymers.

Separation Step b)

In accordance with the invention, the process for producing a terephthalate polyester comprises a separation step b), comprising at least one separation section fed with said depolymerization reaction effluent obtained at the end of the depolymerization step a), in order to obtain at least one glycol effluent and one diester effluent.

Said separation step b) advantageously makes it possible to recover the diol compounds of the glycol feedstock of step a) that have not reacted and the diols compounds possibly released during the depolymerization reaction. Said glycol effluent obtained at the end of said step b) preferably comprises at least 50% by weight, preferentially at least 70% by weight, preferably more than 90% by weight of diol compounds.

Advantageously, said separation section comprises one or more separation operations, in order to enable the recovery of an effluent enriched in diols (referred to as the glycol effluent), and optionally the recovery of an effluent enriched in light impurities and of an effluent enriched in heavy impurities. In particular, the separation section may comprise one or more separation (distillation, stripping, rectification) columns that make it possible to obtain at least one effluent enriched in diols (i.e. the glycol effluent), and optionally an effluent enriched in light impurities and an effluent enriched in heavy impurities. Preferably, said separation section comprises a sequence of gas/liquid separations, preferably from 1 to 5 gas/liquid separations, preferentially between 3 and 5 gas/liquid separations, carried out at a temperature of between 100° C. and 250° C., preferably between 110° C. and 220° C., preferably between 120° C. and 210° C., and at a pressure of between 0.00001 and 0.2 MPa, preferably between 0.00004 and 0.15 MPa, preferably between 0.00004 and 0.1 MPa. Said gas/liquid separations are advantageously stirred by any method known to a person skilled in the art. Under these pressure and temperature conditions, at least one portion of the diol in the reaction effluent, in liquid form, is vaporized at each gas/liquid separation and separated from a liquid stream which comprises the diester monomer, so that the crystallization of the diester monomer and the polymerization thereof are prevented. Advantageously, the temperature and the pressure of the subsequent gas/liquid separation are lower than those of the preceding gas/liquid separation so that at least one portion of the glycol effluent exiting from the preceding separation can, on condensing, reboil a portion of the liquid effluent of the subsequent separation. In this configuration, the supply of heat for recovering the glycol is minimized.

Advantageously, an operation for separating the various diols and possibly dyes, light alcohols or water, possibly within the glycol recovered by the sequence of gas/liquid separations, may be carried out in the separation step b). Thus, the glycol effluent obtained at the end of step b) comprises the diol compound corresponding to the diol unit of the basic unit of the polyalkylene terephthalate of the feedstock of polyester to be recycled, at a content greater than or equal to 50% by weight, preferentially greater than or equal to 70% by weight, preferably greater than or equal to 90% by weight. Preferably, this possible separating operation is carried out in distillation, stripping or rectification columns, and advantageously is carried out at a temperature of between 50° C. and 250° C., preferably between 60° C. and 210° C., preferably between 70° C. and 180° C., and at a pressure between 0.00001 and 0.2 MPa, preferably between 0.00004 and 0.15 MPa, preferably between 0.00004 and 0.1 MPa.

Preferably, all or part of said glycol effluent recovered at the end of step b) is advantageously sent to the treatment step g) of the process according to the invention.

All or part of said glycol effluent recovered at the end of step b) may be prepurified in a section for prepurification of the diols included in step b) in order to remove a portion of the impurities entrained with said glycol effluent, such as, for example, dyes, pigments or other solid particles. The prepurification section fed with all or part of said glycol effluent may comprise, non-exhaustively, an adsorption on a solid (for example on active carbon) and a filtration system. At least one fraction of said prepurified glycol effluent may be directly recycled to the depolymerization step a) and/or to step c) of preparing an esterification feedstock.

The diester effluent obtained at the end of the separation step b), advantageously in liquid form, advantageously comprises more than 10% by weight, preferably more than 25% by weight, preferably more than 50% by weight, of diester monomers and ester oligomers.

The separation section of step b) may possibly advantageously comprise one or more falling film or wiped film evaporation systems, in series or in parallel, carried out at a temperature below or equal to 200° C., preferably below or equal to 180° C., and at a pressure less than or equal to 0.001 MPa, preferably less than or equal to 0.0005 MPa, in order to further reduce the amount of diols possibly remaining in the diester effluent while minimizing the polymerization of the diester monomer in said diester effluent.

Purification Step c)

In accordance with the invention, said diester effluent obtained at the end of the separation step b) then feeds a purification step c), comprising at least one separation section then one discolouration section.

Advantageously, the step of purifying the diester effluent obtained at the end of the separation step b) makes it possible to separate at least one purified diester effluent, from all or some of the following compounds resulting from the depolymerization step a): ester oligomers, possibly unconverted polyester, impurities possibly present in the feedstock of polyester to be recycled, such as other polymers, pigments, dyes, polymerization catalysts or any other inorganic compound making up said feedstock of polyester to be recycled or formed during the depolymerization step a), and if necessary diol compounds not yet separated, while minimizing the loss of diester monomer.

Said purification step thus makes it possible to recover a purified diester effluent with a yield of diester monomer in said purified diester effluent of greater than or equal to 50% by weight, preferably greater than or equal to 70% by weight, preferably greater than or equal to 80% by weight. The expression "yield of diester monomer in said diester effluent" denotes the amount of diester monomer in said diester effluent relative to the total amount of diester monomer introduced into the purification section of step b).

Preferably, the purification step carries out one or more purification operations, such as filtration, evaporation, distillation, adsorption on a trapping mass.

In accordance with the invention, the purification step c) comprises one or more sections for separating the diester effluent obtained at the end of step b), with the objective of separating the diester monomer, which is vaporized, from the heavy impurities, in particular from the oligomers and the polyester possibly not converted in step a) which remain liquid and therefore capture the solid impurities, in particular the pigments, unconverted polymer, other polymers possibly present and polymerization catalysts, while minimizing the loss of diester monomer in particular by re-polymerization. A few ester oligomers may be entrained with the diester monomer.

Said separation section(s) of step c) is (are) advantageously fed by said diester effluent obtained at the end of step b) and operated at a temperature below or equal to 250° C., preferably below or equal to 230° C., and very preferably below or equal to 200° C., at a pressure less than or equal to 0.001 MPa, preferably less than or equal to 0.0001 MPa, preferably less than or equal to 0.00005 MPa, and with a liquid residence time per section of less than or equal to 10 min, preferably less than or equal to 5 min, preferably less than or equal to 1 min. The liquid residence time per section is defined, according to the invention, by the ratio of the liquid volume in said section to the volume flow rate of the hottest stream exiting said section. At the end of said separation section(s) of the purification step c), at least one liquid effluent concentrated in heavy impurities and one prepurified diester effluent, preferably low in impurities, are obtained.

The separation of said prepurified diester effluent and of said liquid effluent concentrated in heavy impurities is advantageously carried out in a system of falling film or wiped film evaporation, by falling film or wiped film short path distillation, or by a succession of several falling film or wiped film short path distillations and/or evaporations, at a temperature below or equal to 250° C., preferably below or equal to 230° C., very preferably below or equal to 200° C., and at a pressure less than or equal to 0.001 MPa, preferably less than or equal to 0.0001 MPa, preferably less than or equal to 0.00005 MPa. The very low operating pressure is necessary in order to be able to carry out said separation at a temperature below or equal to 250° C., preferably below or equal to 230° C., while enabling the vaporization of the diester monomer.

A polymerization inhibitor may advantageously be mixed with the diester effluent obtained at the end of step b), before feeding said purification step c). A flux may also advantageously be mixed with the diester effluent resulting from step b) before feeding said step c), so as to facilitate the removal of the heavy impurities, in particular the pigments, at the bottom of the short path distillation or evaporation system. When it is introduced, the flux must have a boiling point much higher than the diester monomer of the diester effluent under the operating conditions of step c). It can, for example, be polyethylene glycol, or PET oligomers.

The liquid effluent concentrated in heavy impurities advantageously concentrates the oligomers, the unconverted PET and the heavy impurities, in particular the pigments, other polymers optionally present and polymerization catalysts. The operating conditions for the separation in the separation section(s) of said step c) are adjusted so that the loss of diester monomers by re-polymerization is minimized. A few oligomers may be entrained with the diester monomer in the pre-purified diester effluent, in particular in gaseous form.

At least one fraction of said liquid effluent concentrated in heavy impurities may advantageously be recycled to the depolymerization step a) in order to increase the yield of diester monomers of the depolymerization process. Before any recycling operation, said liquid effluent concentrated in heavy impurities advantageously undergoes at least one purification step, preferably a filtration step so as to reduce the amount of pigments and/or other solid impurities optionally present. All or some of said liquid effluent concentrated in heavy impurities may also advantageously be bled from the process and sent to an incineration system or to a pigment recovery system.

The liquid effluent concentrated in heavy impurities may advantageously be mixed with at least one fraction of the glycol effluent obtained at the end of the separation step b) and/or at least one fraction of the purified diol stream obtained at the end of step g) of the process according to the invention, so as to reduce the viscosity of said liquid effluent concentrated in heavy impurities and facilitate the transport thereof to the depolymerization step a), and possibly the treatment thereof in an optional filtration step.

Possibly, the prepurified diester effluent may advantageously be mixed with at least one fraction of the glycol effluent resulting from the separation step b) and/or with at least one fraction of the purified diol stream resulting from step g).

In accordance with the invention, the purification step c) comprises a section for discolouration of the prepurified diester effluent, advantageously operated at a temperature between 100° C. and 250° C., preferably between 110° C. and 200° C., and preferably between 120° C. and 180° C., and at a pressure of between 0.1 and 1.0 MPa, preferably between 0.2 and 0.8 MPa, and preferably between 0.3 and 0.5 MPa, in the presence of an adsorbent, in order to produce a purified diester effluent. Said adsorbent may be any adsorbent known to a person skilled in the art capable of capturing dyes, such as activated carbon or clays, preferably an activated carbon.

The purified diester effluent obtained at the end of step c) comprises at least one diester monomer. It may optionally comprise at least one diol (or glycol), preferably corresponding to the diol unit contained in said diester monomer of said purified diester effluent. Advantageously, the purified diester effluent obtained at the end of step c) comprises at least 10% by weight of diester monomer, preferably at least 20% by weight. It preferably contains less than 1% by weight, preferably less than 0.1% by weight, of the pigments introduced into the process with the feedstock of polyester to be recycled and less than 10% by weight, preferably less than 1% by weight, of the dyes introduced into the process with the feedstock of polyester to be recycled. Preferably, the purified diester effluent obtained at the end of step c) comprises less than 10% by weight, preferentially less than 1% by weight, preferably less than 0.1% by weight of impurities heavier than said diester monomer, optionally other than oligomers of said diester. Very advantageously, the purified diester effluent obtained at the end of step c) is free of colored impurities or of inorganic impurities such as pigments, dyes, depolymerization catalysts and ions. Preferably, the purified diester monomer comprises the molecules of diester monomer and possibly of the oligomers of said diester with a degree of polymerization of between 2 and 5. According to the invention, the term "free of" means that the content of the compound in question in the purified diester effluent is lower than the limit of determination of the analysis method used for determining said content.

Advantageously, the purified diester effluent is obtained at the end of step c) in liquid form. At least one fraction of said purified diester effluent obtained at the end of step c) in liquid form feeds step d) of the process according to the invention. At least one fraction of said purified diester effluent may also be recycled to step a) of the process for producing a terephthalate polyester according to the invention.

Step d) of Preparation of the Polymerization Feedstock

In accordance with the invention, the process for producing a terephthalate polyester comprises a step d) of preparation of a polymerization feedstock. Said step d) comprises at least one mixing section fed with at least one terephthalic feedstock and at least one fraction of said purified diester effluent obtained at the end of step c) in liquid form. Advantageously, said terephthalic feedstock is a terephthalic acid feedstock, which comprises terephthalic acid as compound with a terephthalate unit, or a dimethyl terephthalate feedstock, which comprises dimethyl terephthalate as compound with a terephthalate unit.

In one particular embodiment in which the terephthalic feedstock is a terephthalic acid feedstock comprising terephthalic acid, the polymerization feedstock which is obtained at the end of step d) is a homogeneous two-phase mixture, comprising at least terephthalic acid, a diester monomer and optionally a diol (or glycol). The term "two-phase" is advantageously understood to mean a suspension of a solid phase in a liquid or pasty phase. The term "homogeneous" should be understood as meaning that the solid phase, in suspension in the liquid or pasty phase, is distributed in a homogeneous way throughout the liquid or pasty phase. More particularly, the polymerization feedstock in this embodiment is a mixture of solid terephthalic acid particles, with a diameter typically of between 1 and 1000 μm, in particular between 80 and 300 μm, homogeneously distributed in a liquid or pasty phase comprising the diester monomer.

In another particular embodiment in which the terephthalic feedstock is a dimethyl terephthalate feedstock comprising dimethyl terephthalate, the polymerization feedstock, comprising at least dimethyl terephthalate, a diester monomer and optionally a diol (or glycol) feedstock, is advantageously a single-phase mixture.

Advantageously, the amounts of said terephthalic feedstock, and of purified diester effluent, introduced into said mixing section, are adjusted so that the ratio of the total number of moles of diol units of formula —$[C_{(n+1)}H_{(2n+2)}O_2]$—, n being an integer greater than or equal to 1, preferably between 1 and 5, preferentially between 1 and 3, introduced into said mixing section, relative to the total number of moles of terephthalate units of formula —$[CO—(C_6H_4)—CO]$— introduced into said mixing section, is between 1.0 and 2.0, preferably between 1.0 and 1.5, preferentially between 1.0 and 1.3.

According to one embodiment of the invention, said mixing section of said step d) of the process according to the invention is further fed with a diol monomer feedstock, preferably comprising a diol monomer of chemical formula HO—$C_{(n+1)}H_{(2n+2)}$—OH, n being an integer greater than or equal to 1, preferably between 1 and 5, preferably between 1 and 3. Preferably, said diol monomer feedstock comprises at least 90 mol %, preferentially at least 95 mol %, very preferably 98 mol %, of a diol monomer incorporated into the composition of the individual unit of the terephthalate polyester targeted. Preferably, the diol monomer feedstock comprises ethylene glycol, preferably at a content greater than or equal to 90 mol %, at least 95 mol %, preferentially at least 98 mol %. The diol of said diol monomer feedstock may have a different chemical structure to or the same chemical structure as, preferably the same chemical structure as, that of the diol monomer incorporated into the composition of the feedstock of polyester to be recycled of the depolymerization step a). Preferably, said diol monomer feedstock may be, at least in part, a fraction of the purified diol stream obtained in step g) of the process according to the invention and/or at least in part a fraction of the glycol effluent obtained at the end of step b) of the process according to the invention.

When a diol monomer feedstock is incorporated in the mixing section of step d), the amount of said diol feedstock introduced into the mixing section of step d) is adjusted so that the ratio of the number of diol units relative to the number of terephthalate units in the mixture of step d), as defined above, is between 1.0 and 2.0, preferably between 1.0 and 1.5, preferentially between 1.0 and 1.3.

Advantageously, the amount of molecules of diester monomer of the purified diester effluent introduced into the mixing section of step d) represents at least 5% by weight, relative to the weight of terephthalic acid (PTA), or dimethyl terephthalate (DMT), preferably at least 15% by weight.

Insofar as a molecule of diester monomer comprises two diol units and one terephthalate unit, a molecule of terephthalic acid or of dimethyl terephthalate comprises one terephthalate unit and a molecule of diol comprises one diol unit, the incorporation of one mole of diester monomers, for example one mole of bis(2-hydroxyethyl) terephthalate (BHET), as a mixture with the terephthalic acid or dimethyl terephthalate monomer feedstock and diol monomer feedstock, such as ethylene glycol, makes it possible to replace a portion of said terephthalic feedstock and all or some of said diol feedstock.

Advantageously, the mixing of said terephthalic feedstock, of at least one fraction of said purified diester effluent and optionally of said diol monomer feedstock is carried out in any equipment known to a person skilled in the art and that enables an effective mixing. In the particular embodiment in which the polymerization feedstock comprises terephthalic acid, step d) makes it possible to obtain a homogeneous distribution of the solids in suspension in the liquid mixture or the paste. Preferably, the mixing of step d) of the process according to the invention is carried out in a mixer with mechanical stirring or that is stirred by recirculation of a liquid or of said mixture, for example using a pump that circulates the mixture in a loop.

Said terephthalic feedstock, the fraction of said purified diester effluent and optionally said diol monomer feedstock are introduced together or separately into the mixer.

Advantageously, said mixing section in step d) of the process according to the invention is operated at a temperature of between 25° C. and 250° C., preferably between 60° C. and 200° C., preferably between 100° C. and 150° C., and at a pressure of greater than or equal to 0.1 MPa. The pressure of said mixing section is very advantageously less than or equal to 5 MPa.

One or more polymerization catalysts may, in addition, be incorporated in the mixture of step d) of the process according to the invention.

Other monomer (or comonomer) compounds can also advantageously be introduced into the mixture and be found in the esterification feedstock. Non-exhaustively, said other monomer compounds can be dicarboxylic acids, such as, for example, isophthalic acid, and diols, such as, for example, 1,4-dihydroxymethylcyclohexane and diethylene glycol.

According to one of the particular embodiments of the invention in which a terephthalic acid feedstock is used, the incorporation of a diester monomer, for example BHET monomers, in the polymerization feedstock, makes it possible to replace a portion of the terephthalic acid, which is a compound in the form of a powder of solid particles, in the two-phase mixture of the monomers for the production of polyester. This replacement of a portion of the terephthalic acid and all or some of the diol with diester monomers, in the process according to the invention, makes it possible, at an identical solids content of the two-phase mixture relative to that of the conventional polyester production processes, to significantly reduce the amount of diol, for example ethylene glycol, introduced in excess into the mixture, leading to a reduction in the costs, in particular of raw materials, but also a sizeable reduction in the energy consumptions of the polyester production process, owing to the reduction in the amount of dial to be recovered during the polymerization, to be treated and to be recycled.

Condensation Step e)

In accordance with the invention, the process for the production of a terephthalate polyester comprises a step e) of condensation of the polymerization feedstock obtained at the end of step d), in order to produce at least one condensation reaction effluent, one diol effluent and one aqueous effluent or one methanol effluent. Said condensation step e) comprises at least one reaction section and at least one separation section.

In the particular embodiment in which the terephthalic feedstock is a terephthalic acid feedstock, the reaction carried out in step e) advantageously comprises an esterification reaction which consists of a condensation reaction of at least the hydroxyl (—OH) groups of the diester monomers of the fraction of the purified diester effluent, produced in step c) and incorporated at least partly in the polymerization feedstock in step d), and of the diol monomers optionally present in the polymerization feedstock with at least the carboxyl (—COOH) groups of the terephthalic acid of the terephthalic acid feedstock incorporated in the polymerization feedstock in step d). This esterification reaction produces molecules of diester monomer, for example bis(2-hydroxyethyl) terephthalate (BHET), and diester oligomers advantageously comprising from 2 to 5 terephthalate units. It also releases water. The reaction carried out in step e) of the process according to the invention also advantageously comprises transesterification reactions consisting of the condensation reaction of molecules of diester monomer with one another, thus releasing diol molecules.

In the other particular embodiment in which the terephthalic feedstock is a dimethyl terephthalate feedstock, the reaction carried out in step e) advantageously comprises a transesterification reaction which consists of a condensation reaction of at least the hydroxyl (—OH) groups of the diester monomers of the fraction of the purified diester effluent, produced in step c) and incorporated at least partly in the polymerization feedstock in step d), and of the diol monomers optionally present in the polymerization feedstock with at least the carboxylate (—COO—) groups of the dimethyl terephthalate of the dimethyl terephthalate feedstock incorporated in the polymerization feedstock in step d). This transesterification reaction produces molecules of diester monomer, for example bis(2-hydroxyethyl) terephthalate (BHET), and diester oligomers advantageously comprising from 2 to 5 terephthalate units. It also releases methanol. The reaction carried out in step e) of the process according to the invention also advantageously comprises transesterification reactions consisting of the condensation reaction of molecules of diester monomer with one another, thus releasing diol molecules.

Advantageously, said reaction section is operated in one or more reactors in series or in parallel, at a temperature between 150° C. and 400° C., preferably between 200° C. and 300° C., at a pressure between 0.05 and 1 MPa, preferably between 0.1 and 0.3 MPa, with a residence time between 0.5 and 10 h, preferably between 1 and 5 h. According to the invention, the residence time in said esterification step d) is defined as the ratio of the reaction volume of a reactor of said reaction section to the volume flow rate of the liquid stream exiting from said reactor.

Advantageously, a polymerization catalyst known to a person skilled in the art may optionally be introduced, optionally as a mixture with a diol stream, into the reaction section of the condensation step e), in particular in the case of an esterification reaction starting from a polymerization feedstock. The polymerization catalysts are non-exhaustively catalysts based on antimony, tin, germanium or aluminium, acetate of zinc, calcium or manganese. In the particular embodiment in which the polymerization feedstock comprises the dimethyl terephthalate feedstock, a transesterification catalyst known to a person skilled in the art is optionally added into the reaction section of step e), advantageously as a mixture with a diol stream.

The condensation reactions are advantageously carried out in one or more stirred reactors, in one or more tubular reactors or in a combination of stirred and tubular reactors.

Advantageously, the reaction section also comprises at least one withdrawal of a withdrawn effluent rich in water or in methanol, and in diol. The water or the methanol and the diol within said withdrawn effluent are separated in the separation section of step e). The latter is fed with said withdrawn effluent, rich in water or methanol and in diol, and advantageously produces an aqueous, or methanol, effluent and a diol effluent. Advantageously, the water, or the methanol, is separated by difference in volatility, for example by distillation, or by adsorption starting from said withdrawn effluent containing at least a portion of the diol and of the water or methanol released present in the reaction medium.

Advantageously, at least one fraction of said diol effluent obtained in step e) of the process according to the invention may optionally be sent to step g) for treating the diols or send back directly to the reaction section of said step e). Preferably, said diol effluent obtained at the end of the separation section of step e) is sent back directly to the reaction section of said step e). Said condensation reaction effluent obtained at the end of said step e), in particular at the outlet of the reaction section of step e), comprises diester monomers and ester oligomers. Preferably, the diester monomers in said condensation reaction effluent are of the same type as the diester monomers of the liquid purified diester effluent obtained in step c) and incorporated at least in part into the mixture of step d). Preferably, the ester oligomers in said condensation reaction effluent are advantageously composed of basic units corresponding to the basic repeating units of the terephthalate polyester targeted by the process according to the invention.

The incorporation of at least one fraction of the purified diester effluent in the monomer feedstocks of the polymerization makes it possible to replace at least a part of the terephthalic feedstock and all or part of the diol feedstock, thus making it possible to reduce the amount of water or methanol released and therefore to limit the amount of aqueous or methanol effluent, withdrawn from the reaction medium and to be treated. The energy consumption is advantageously decreased thereby.

Polycondensation Step f)

In accordance with the invention, the process for producing a terephthalate polyester comprises a step f) of polycondensation of the condensation reaction effluent obtained in step e), in order to obtain at least said terephthalate polyester and a diol effluent. Said diol effluent comprises at least one diol monomer advantageously corresponding to the diol unit of formula —$[C_{(n+1)}H_{(2n+2)}O_2]$—, n being an integer greater than or equal to 1, preferably between 1 and 5, preferentially between 1 and 3, of the diester monomer of the purified diester effluent which feeds, at least in part, the mixing section of step d) of the process according to the invention.

The polycondensation step f) consists in carrying out a condensation reaction between the diester monomers and ester oligomers of the condensation reaction effluent obtained in step e), in order to obtain a polyester with a given degree of polymerization and the desired physicochemical properties (for example: viscosity index, crystallinity, colour, mechanical properties, and the like). Said condensation reaction releases diol compounds, possibly water or methanol and coproducts, which it is advisable to remove.

The polycondensation step f) comprises at least one reaction section comprising least one reactor in which the polycondensation reaction is carried out and at least one withdrawal of a diol effluent, comprising at least one diol monomer, advantageously corresponding to the diol unit of formula —[$C_{(n+1)}H_{(2n+2)}O_2$]—, n being an integer greater than or equal to 1, preferably between 1 and 5, preferentially between 1 and 3, of the diester monomer of the purified diester effluent.

Advantageously, said reaction section of step f) is operated, in one or more reactors, functioning in series or in parallel, at a temperature between 200° C. and 400° C., preferably between 250° C. and 300° C., at a pressure between 0.0001 and 0.1 MPa, preferably between 0.0004 and 0.01 MPa, with a residence time between 0.1 and 5 h, preferably between 0.5 and 3 h. According to the invention, the residence time in said polycondensation step f) is defined as the ratio of the reaction volume of a reactor of said reaction section to the volume flow rate of the liquid stream exiting from said reactor. The polycondensation reaction of step f) may be carried out in two successive reaction steps: a melt-phase condensation step, followed by a solid-phase post-condensation step.

Advantageously, polymerization additives and catalysts can be introduced into the polycondensation step f). Non-exhaustively, the additives can comprise agents which inhibit the etherification side reactions, such as, for example, amines (n-butylamine, diisopropylamine or triethylamine), sodium hydroxide or organic hydroxides or lithium carbonate, stabilizing agents, such as phosphites or phosphates, and compounds of polyamide type for reducing the amount of decomposition product, such as acetaldehyde. The polymerization catalysts commonly used are, such as, for example, catalysts based on antimony, titanium, germanium or aluminium, acetate of zinc, calcium or manganese.

Advantageously, the withdrawal of said diol effluent is carried out using one or more withdrawal system(s), advantageously connected to the reactor(s) of the reaction section of said step f), and makes it possible to separate the diol monomer released during the polycondensation reaction and possibly the water or methanol, and other coproducts possibly released during the condensation reaction. Preferably, the diol effluent, withdrawn from the reactor(s) of step f), is withdrawn in gaseous form and is then advantageously cooled to a temperature between 0 and 100° C. and condensed in order to obtain a liquid diol effluent.

Preferably, at least one fraction of the liquid diol effluent is sent to step g) of the process according to the invention. At least one fraction of said liquid diol effluent may also be recycled directly to step d) of preparation of a polymerization feedstock. In a very particular embodiment, said liquid diol effluent may be completely or partly recycled directly to the condensation step e).

Step g) of Treating the Diols

In accordance with the invention, the process for producing a terephthalate polyester comprises a step g) of treating the diols, comprising a recovery section fed at least by all or part of the glycol effluent resulting from step b) and all or part of the diol effluent resulting from step f), in order to obtain a diol stream to be treated, and a section for purification of said diol stream to be treated in order to obtain a purified diol stream.

Said recovery section of step g) may further be possibly fed by at least one fraction of the diol effluent resulting from the condensation step e) and/or an external supplement of diol. Advantageously, the recovery section may comprise one or more filtration operations.

Said diol stream to be treated obtained at the end of the recovery section of step g) is sent to the purification section of step g) in order to obtain a purified diol stream.

Said purification section comprises at least one separation system that carries out any method of physical, physicochemical or chemical separation known to a person skilled in the art, such as, for example, gas/liquid separation, distillation or adsorption. Preferably, the purification of said diol effluent to be treated employs at least one distillation column, preferably a series of distillation columns, operated at a temperature between 50° C. and 250° C., preferably between 70° C. and 220° C., and at a pressure between 0.001 and 0.2 MPa, preferably between 0.01 and 0.1 MPa. Preferably, said purification section comprises a phase of separation of the impurities which are lighter than the diol monomer within the diol stream to be treated and a phase of separation of the impurities which are heavier than the diol monomer within the diol stream to be treated, preferably in a series of distillation columns.

Advantageously, said step g) may also comprise a section for removal of the volatile organic compounds by thermal or catalytic combustion of said compounds in order to prevent them from being discharged to the environment. Non-exhaustively, said section for treatment of the impurities comprises a filtration if presence of solid particles and a catalytic or non-catalytic combustion system.

Said purified diol stream obtained at the end of step g) of the process according to the invention may then be sent, completely or partly, to at least steps a) and d) of the process according to the invention.

The process according to the invention thus makes it possible to obtain a terephthalate polyester, advantageously having the targeted degree of polymerization and the desired physicochemical properties, from polyester material to be recycled resulting from collecting and sorting industries, while limiting the consumption of "fresh" raw material and the overall energy consumption. The reduction in energy consumption is enabled in particular owing to a system of optimized recycling of the diol(s), the diol released in particular during the polymerization and the diol possibly introduced into the mixture of monomers for the polymerization (i.e. into the polymerization feedstock) and which has not been converted.

The process according to the invention, at the end of steps a), b) and c), also makes it possible, very advantageously, to produce an intermediate stream comprising a terephthalic acid diester (such as for example BHET) and having a high purity compatible with the specifications required by the polymerization processes in order to obtain a terephthalate polyester, it being possible for said liquid diester intermediate stream to be injected directly into the so-called polymerization steps, in particular directly incorporated into a mixture of monomer feedstocks feeding the polymerization sections, preferably as a replacement for at least one portion of said monomer feedstocks. The direct injection of said diester intermediate stream makes it possible to have a lower energy consumption than the sum of a depolymerization process and a polymerization process. Preferably, the terephthalic acid diester is bis(2-hydroxyethyl) terephthalate (BHET) resulting from the glycolysis of PET by ethylene glycol.

The process according to the invention makes it possible to respond to an ecological demand, since it enables the recycling of plastic that until now has been difficult to recycle, such as opaque PET.

The following FIGURES and examples illustrate the invention without limiting the scope thereof.

BRIEF DESCRIPTION OF THE DRAWINGS

FIG. 1 depicts one particular configuration of a process for producing polyethylene terephthalate (PET) according to the invention, integrating a scheme for depolymerization, preferably by glycolysis, of a feedstock of PET to be recycled and a scheme for polymerization of a mixture comprising the intermediate purified BHET stream obtained from the depolymerization process, terephthalic acid and monoethylene glycol diol (or ethylene glycol, MEG).

The glycolysis process of FIG. 1 comprises the sequence of the depolymerization step a), then separation step b), then purification step c).

The depolymerization step a) is fed by at least said feedstock of PET to be recycled (1) and a MEG feedstock (3c). Advantageously, said feedstock of PET to be recycled is preheated and pressurized under the operating conditions of said step a). Advantageously, at least 80% by weight of the feedstock is introduced into step a) in liquid form, very advantageously at least 90% by weight, preferentially at least 95% by weight. The temperature of the feedstock of PET to be recycled is advantageously between 225° C. and 275° C. The time needed for the introduction and the associated temperature are adjusted so as to minimize the thermal degradation of the polyester.

Advantageously, said step a) comprises a screw conveying section, referred to as extrusion section, fed by said feedstock of PET to be recycled. The residence time in said extrusion section, defined as the volume of said section divided by the volume flow rate of feedstock is advantageously less than 15 min, preferably less than 10 min, and preferably less than 2 min. Said extrusion section is advantageously connected to a vacuum extraction system so as to remove impurities such as dissolved gases, light organic compounds and/or moisture present in the feedstock of PET to be recycled. Said extrusion section can also advantageously comprise a filtration system in order to remove solid particles with a size of greater than 40 μm, preferably with a size of between 3 and 40 μm, such as sand particles.

The feedstock of PET to be recycled is advantageously brought into contact with at least one fraction of the MEG effluent (3c) resulting from step b), advantageously within said extrusion section, also referred to as reactive extrusion section. The MEG stream (3c) may advantageously be superheated prior to being fed into step a), in order to make it easier to bring the feedstock of PET to be recycled to temperature. The number of moles of MEG resulting from step b) per mole of diester in said feedstock of PET to be recycled is advantageously less than or equal to 1.0 and preferably less than or equal to 0.5.

Said step a) may also advantageously be fed with a fraction of the effluent (5) resulting from step c), said fraction comprising a mixture of unconverted oligomers and polyester and preferentially having been purified in a filtration step.

The depolymerization step a) comprises a reaction section operated, in one or more reactors, at a temperature of between 150° C. and 400° C., preferably between 180° C. and 300° C., preferably between 200° C. and 280° C., in the liquid phase, with from 1 to 20 mol of MEG per mole of diester in said feedstock of PET to be recycled, preferably from 3 to 15 mol per mole, and preferably from 5 to 10 mol per mole, a residence time of between 0.1 and 6 h, preferably between 0.5 and 4 h, and an operating pressure of at least 0.1 MPa, preferentially at least 0.4 MPa. Preferably, said depolymerization step is carried out without addition of catalyst.

The glycolysis reaction makes it possible to convert the feedstock of PET to be recycled to give bis(2-hydroxyethyl) terephthalate (BHET) monomer and BHET oligomers. The conversion of the feedstock of PET to be recycled in said depolymerization step is greater than 50%, preferably greater than 70%, preferably greater than 85%. The molar BHET yield is greater than 50%, preferably greater than 70%, in a preferred way greater than 85%. The molar BHET yield corresponds to the molar flow rate of BHET at the outlet of said step a) over the slow rate of moles of diester units in the feedstock of PET to be recycled (1).

An internal recirculation loop is also advantageously used in step a). It comprises the withdrawal of a fraction of the reaction system (i.e. all of the constituents and phases present within said reaction section), the filtration of this fraction, and the reinjection of said fraction into said step a). This internal recirculation loop advantageously makes it possible to remove the solid impurities possibly within the reaction liquid.

The reaction effluent (2) resulting from the depolymerization step a) feeds step b) for separation of the MEG, which is operated at a pressure lower than that of step a) so as to vaporize a fraction of the reaction effluent (2) to give at least one gaseous MEG effluent comprising more than 50% by weight of MEG, preferably more than 70% by weight, preferably more than 90% by weight, and a liquid effluent rich in BHET monomers (4).

Step b) advantageously comprises a sequence of gas/liquid separations, advantageously from 1 to 5, very advantageously from 3 to 5 successive gas/liquid separations, carried out at a temperature of between 100° C. and 250° C., preferably between 110° C. and 220° C., preferably between 120° C. and 210° C. The liquid effluent from the preceding separator feeds the subsequent separator. The liquid effluent resulting from the final gas/liquid separation constitutes the liquid effluent rich in BHET monomers (4). At least one fraction of the gaseous MEG effluents recovered is condensed to give liquid MEG effluents.

The temperature and the pressure of the subsequent separator are lower than those of the preceding separator so that at least one portion of the gaseous MEG effluent exiting from the preceding separation can, on condensing, reboil a portion of the liquid effluent of the subsequent separation. In this configuration, the supply of heat for recovering the MEG is minimized.

Step b) is carried out so that the temperature of the liquid effluents is kept above the precipitation temperature of the BHET monomer, and below a high value, depending on the diol/monomer molar ratio, above which the BHET monomer significantly repolymerizes. The temperature in the gas/liquid separation sections of step b) is between 100° C. and 250° C., preferably between 110° C. and 220° C., preferably between 120° C. and 210° C. The pressure in the gas/liquid separators of step b) is adjusted to enable the evaporation of the MEG and of the impurities possibly present in the reaction effluent (2) at a temperature that minimizes repolymerization and that enables optimal energy integration. It is generally between 0.00001 and 0.2 MPa, preferably between 0.00004 and 0.15 MPa, preferably between 0.00004 and 0.1 MPa.

The gaseous and liquid MEG effluents resulting from said gas/liquid separations may contain other compounds such as dyes, light alcohols, water, diethylene glycol. Step b) advantageously comprises one or more sections for fractionating all or some of said gaseous and liquid MEG effluents to give at least an effluent rich in light impurities (3a), an effluent rich in heavy impurities (3b) and an MEG effluent (3c), and that is (are) operated at a temperature of between 50° C. and 250° C., preferably between 60° C. and 210° C., preferably between 70° C. and 180° C., at a pressure of between 0.00001 and 0.2 MPa, preferably between 0.00004 and 0.15 MPa, preferably between 0.00004 and 0.1 MPa. Preferably, the fractionation of said gaseous and liquid MEG effluents is carried out in distillation, stripping or rectification columns. Advantageously, all or some of said MEG effluents may be treated in a prepurification step, upstream or downstream of said fractionating sections, in order to remove the dyes for example via adsorption on a solid (for example activated carbon).

The MEG effluent (3c) advantageously contains more than 99% by weight of MEG, preferably more than 99.5% by weight of MEG. All or some of the MEG effluent (3c) is advantageously recycled to step a), advantageously as a mixture with at least one fraction of the purified MEG effluent resulting from the recovery step g) of the polymerization process.

The effluent rich in light impurities (3a) and the effluent rich in heavy impurities (3b) are advantageously sent to the recovery step g) of the polymerization process.

The liquid effluent rich in BHET monomers (4) feeds the purification step c). Step c) comprises one or more sections for separation of the liquid effluent rich in BHET monomers (4) to give a liquid effluent rich in heavy impurities (5) and a prepurified BHET effluent, which is (are) operated at a temperature below 250° C., preferably below 230° C. and very preferably below 200° C., and a pressure of less than 0.001 MPa, preferably of less than 0.0001 MPa, preferably less than or equal to 0.00005 MPa, with a liquid residence time of less than 10 min, preferably of less than 5 min, preferably less than 1 min.

The liquid effluent concentrated in heavy impurities (5) advantageously concentrates the oligomers, the unconverted PET and the heavy impurities, in particular the pigments, other polymers optionally present and polymerization catalysts. The operating conditions for the separation in said step c) are adjusted so that the loss of BHET monomers by re-polymerization is minimized. A few oligomers may be entrained with the monomer in the gaseous prepurified BHET effluent.

The separation of said prepurified BHET effluent is advantageously carried out in a system of falling film or wiped film evaporation or by falling film or wiped film short path distillation, or a succession of several falling film or wiped film short path distillations and/or evaporations. The very low operating pressure is necessary in order to be able to carry out said separation at a temperature below 250° C., preferably below 230° C., while enabling the vaporization of the monomer.

A fraction of said effluent concentrated in heavy impurities (5) may advantageously be recycled to the depolymerization step a) in order to increase the BHET yield of the depolymerization process.

Said heavy impurities effluent (5) advantageously undergoes at least one purification step, preferably a filtration step, prior to the recycling thereof, so to reduce the amount of pigments and/or other solid impurities. All or some of said heavy impurities effluent (5) may also advantageously be bled from the process and sent to an incineration system or to a pigment recovery system.

A fraction of the MEG effluent (3c) or of the purified MEG effluent (15) resulting from step g) or a mixture of a fraction of said effluents may advantageously be mixed with the effluent concentrated in heavy impurities (5) resulting from step c) so as to reduce the viscosity of said heavy impurities effluent and to facilitate the transportation thereof to step a), and possibly the treatment thereof in an optional filtration step.

Step c) comprises one or more sections for discolouration of the prepurified BHET effluent, operated at a temperature between 100° C. and 250° C., preferably between 110° C. and 200° C., and preferably between 120° C. and 180° C., and at a pressure of between 0.1 and 1.0 MPa, preferably between 0.2 and 0.8 MPa, and preferably between 0.3 and 0.5 MPa, in the presence of an adsorbent and producing a purified BHET effluent (6). Said adsorbent can be any adsorbent known to a person skilled in the art capable of capturing dyes, such as activated carbon or clays, advantageously an activated carbon.

The prepurified BHET effluent is advantageously mixed with a fraction of the MEG effluent (3c) resulting from step b) or with a fraction of the purified MEG effluent resulting from step g).

The purified BHET effluent (6) obtained at the end of step c) of the depolymerization process advantageously comprises more than 50 mol % of MEG, preferably more than 60 mol %, preferably more than 70 mol %.

The purified BHET effluent (6) advantageously feeds a feedstock preparation step d). It is mixed, in step d), with at least one terephthalic acid feedstock (7), possibly with a portion of the MEG effluent (15) resulting from step g) and optionally co-monomers (8).

The feedstock preparation step d) is carried out at a temperature preferably above 80° C., preferably above 110° C.

In the case where a depolymerization unit is attached to a pre-existing polymerization unit, the amount of BHET monomer resulting from the purified BHET effluent (6) may advantageously represent less than 30 mol % of the total amount of aromatic monomer comprising terephthalic acid, the BHET in the mixture prepared in step d) of the polymerization process, preferably less than 25 mol %, preferably less than 20 mol %, which makes it possible to ensure an optimal integration by minimizing the investment in the depolymerization unit and the modifications to be made to the polymerization unit.

The polymerization process also comprises at least an esterification step e), a polycondensation step f) and a step g) for recovery and purification of the MEG effluents.

The polymerization process is preferably a process that is already operating, i.e. already operated with feedstocks of PTA and MEG monomers, optionally co-monomers before the integration of the process for depolymerization of PET to be recycled. The integration of the depolymerization process in said particular configuration of the process according to the invention makes it possible to incorporate PET to be recycled in virgin PET without any impact on the properties of the final PET produced while minimizing the impacts on the configuration of the polymerization process and the energy consumption owing to an optimized integration of the depolymerization process with steps d), e) and g) of the polymerization process, and also owing to the performance and low energy consumption of said depolymerization process. The esterification step e) is fed by the mixture (9) resulting from step d). The esterification reaction comprises a reaction section operated, in one or more reactors, at a temperature between 150° C. and 400° C., preferably between 200° C. and 300° C., at a pressure between 0.05 and 1 MPa, preferably between 0.1 and 0.3 MPa, and a residence time between 1 and 10 h, preferably between 1.5 and 5 h.

The water produced by the esterification reaction is advantageously separated by at least one water separation system within step e), preferably by distillation, in order to produce an aqueous stream (10).

The reaction effluent (11) then feeds the polycondensation step f). Said step f) is advantageously fed with a polymerization catalyst and additives (14) preferably as a mixture with a fraction of the purified MEG effluent (15) resulting from step g).

The polycondensation step f) comprises at least one reaction section in order to produce a polyester stream (12) and at least one withdrawal making it possible to separate at least one effluent (13) containing MEG, water and other co-products released during the condensation reactions. Said effluent (13) is advantageously sent to step g) for recovery and purification of the MEG effluents.

The reaction section of the polycondensation step f) comprises one or more reactors operated at a temperature between 200° C. and 400° C., preferably between 250° C. and 300° C., at a pressure between 0.0001 and 0.1 MPa, preferably between 0.0004 and 0.01 MPa, and a residence time between 0.1 and 5 h, preferably between 0.5 and 3 h.

Step g) for recovery and purification of the MEG effluents advantageously recovers the effluent (13) resulting from step f) of the polymerization process and the effluents (3a) and (3b) resulting from step b) of the depolymerization process.

Said step g) comprises one or more separation sections, preferably one section for separation of impurities lighter than MEG and one section for separation of impurities heavier than MEG. Preferably, the purification of said MEG effluents is carried out by a series of two distillation columns operated at a temperature between 50° C. and 250° C., preferably between 70° C. and 220° C. and at a pressure between 0.001 and 0.2 MPa, preferably between 0.01 and 0.1 MPa. The effluent (3a) rich in light impurities is advantageously mixed with the effluent (13) then sent to a first distillation column that makes it possible to separate the light impurities (16), in particular water, from an MEG effluent which is then advantageously sent as a mixture with the effluent (3b) rich in heavy impurities to a second distillation column in order to recover a purified MEG effluent (15) and an effluent of heavy impurities (17).

The performance of the depolymerization process that minimizes the production of light and heavy impurities, and the pre-fractionation carried out advantageously in step b) of said depolymerization process makes it possible to feed the separation columns of step g) of the polymerization process with a minor impact on the initial configuration thereof.

EXAMPLES

Example 1—Comparative

Production of Virgin PET in a PET Polymerization Process 5.5 t/h of terephthalic acid (PTA) are introduced into a mixing vessel equipped with mechanical stirring and mixed at 110° C. with 2.5 t/h of a monoethylene glycol (MEG) stream comprising 2.13 t/h of MEG originating from a storage tank and 0.37 t/h of recycled MEG originating from the section for the purification of the MEG.

The amounts of PTA and MEG introduced correspond to a PTA/MEG molar ratio of 1.23.

At 110° C., the solids content by volume, defined as the ratio of the volume of solid to the total volume of the paste (solid+liquid), is 60.7% by volume. The mixture obtained forms a viscous paste.

The mixture obtained is subsequently transferred, using an appropriate pump, to a first esterification reactor operated at 260° C., 5 bara (i.e. 0.5 MPa) with a residence time of 1.25 h. 1.4 t/h of a vapour effluent comprising 71% by weight of water and 29% by weight of MEG are withdrawn and sent into a reflux column in order to separate the water formed by the esterification reaction and the MEG. The latter is subsequently returned to the reactor. A conversion of the PTA of 85% is obtained in the first reactor.

The liquid effluent from the first reactor is subsequently sent into a second esterification reactor operated at 260° C. and 2 bara (i.e. 0.2 MPa) with a residence time of 1.25 h. 140 kg/h of a vapour effluent comprising 40% by weight of water and 60% by weight of MEG is withdrawn from the second reactor and sent to the reflux column. A conversion of the PTA of 92% is achieved at the outlet of the second reactor.

The liquid effluent from the second esterification reactor is sent into a third reactor operated at 275° C. and 33 mbar (i.e. 0.033 MPa) with a residence time of 0.5 h which makes it possible to drive the conversion of the PTA to 95.8% and to initiate the polycondensation. Antimony trioxide is added as polymerization catalyst at the inlet of the third reactor in a proportion of 220 ppm by weight. A vapour effluent comprising 70% by weight of MEG, 16.5% by weight of water, 5.5% by weight of acetaldehyde, 2.5% by weight of diethylene glycol and 5.5% by weight of oligomers is withdrawn from the third reactor and partially condensed and then sent to the section for purification of the MEG.

The liquid effluent from the third reactor is sent into a fourth reactor (polycondensation reactor) operated at 275° C. and 66 mbar (i.e. 0.0066 MPa) with a residence time of 0.5 h. A vapour effluent with the composition 60% by weight of MEG, 25% by weight of water, 6% by weight of acetaldehyde, 3% by weight of diethylene glycol and 6% by weight of oligomers is withdrawn from the fourth reactor and partially condensed and then sent to the section for purification of the MEG.

The liquid effluent from the fourth reactor is sent into a final reactor (polycondensation reactor) operated at 280° C. and 1.3 mbar (i.e. 0.000013 MPa) with a residence time of 1 h. A vapour effluent with the composition 57% by weight of MEG and 43% by weight of water is withdrawn and partially condensed and then sent to the section for purification of the MEG.

The section for purification of the MEG comprise a first distillation column provided with 25 plates operated at the top at 145° C. and 200 mbar (i.e. 0.02 MPa), making it possible to separate the diethylene glycol. The bottom product from the first distillation column is sent into a second distillation column provided with 17 plates operated at the top at 100° C. and 1 bara (i.e. 0.1 MPa), making it possible to separate the light components, such as the water and the acetaldehyde. The MEG recovered at the end of these 2 distillations exhibits a purity of greater than 99.8% and is subsequently recycled to the mixing vessel.

6.25 t/h of PET are produced. The overall primary energy consumption of the production of PET is 5.8 MMkcal/h.

Production of Discoloured and Depigmented Solid BHET and Incorporation of at Least One Fraction in the PET Polymerization Process 4 t/h of flakes resulting from a ground and washed feedstock of PET to be recycled, consisting of 50% by weight of opaque PET and 50% by weight of coloured PET, are melted in an extruder at 250° C. and mixed with 11.4 t/h of ethylene glycol (MEG). The mixture obtained is injected into a stirred reactor, maintained at 220° C. and at a pressure of 4 bara (i.e. 0.4 MPa), for a residence time of 4 h. At the outlet of the reactor, the reaction effluent comprises 66% by weight of MEG, 27.4% by weight of BHET, 1.7% by weight of diethylene glycol (DEG), 0.2% by weight of water and 4.7% by weight of oligomers, pigments and other heavy compounds.

The ethylene glycol present in the reaction effluent is separated by evaporation in a sequence of 5 vessels at temperatures ranging from 200° C. to 124° C. and pressures from 0.1 MPa to 0.00025 MPa. At the end of this evaporation step, an MEG stream of 10.95 t/h, composed of 97% by weight of MEG, 2.5% by weight of DEG, 0.2% by weight of water and 0.2% by weight of BHET, and a liquid stream rich in BHET of 5.17 t/h are recovered. The MEG stream is sent into a first distillation column provided with 25 plates and operated at the top at 200 mbar (i.e. 0.02 MPa) and 145° C., in order to separate the DEG and heavy products, then into a second distillation column provided with 17 plates and operated at the top at 100° C. and 1 bara (i.e. 0.1 MPa), in order to separate the water and to recover a purified MEG effluent which can subsequently be recycled to the depolymerization reactor as a mixture with a supplement of fresh MEG. The liquid stream rich in BHET comprises 87.1% by weight of BHET, 0.2% by weight of MEG, 0.1% by weight of DEG and 12.6% by weight of oligomers, pigments and other heavy compounds.

The liquid stream rich in BHET is subsequently injected into a short path distillation at a temperature of 205° C. and a pressure of 0.2 mbar (i.e. 0.00002 MPa). A prepurified BHET liquid effluent with a flow rate of 4.46 t/h is recovered by cooling the vapours in the short path distillation to 115° C. It comprises 99.8% by weight of BHET, 0.1% by weight of MEG and 0.1% by weight of DEG. A heavy residue comprising 93% by weight of oligomers, pigments and other heavy compounds and 7% by weight of BHET is also recovered at a flow rate of 0.7 t/h at the outlet of the short path distillation.

The prepurified BHET liquid stream is compressed up to 0.5 MPa and heated to 150° C. then feeds a fixed bed of activated carbon having an adsorption capacity equal to 5% of its weight. At the end of this step, a discoloured and depigmented BHET liquid stream is recovered. It is then cooled and solidified at 40° C.

The overall primary energy consumption of the depolymerization is 1.25 MMkcal/t BHET.

A fraction of the discoloured and depigmented solid BHET is reinjected into a step for preparing the mixture of the monomers of the PET polymerization process similar to the polymerization process described above with a view to producing 6.25 t/h of PET in total. The polymerization process followed is identical to the one described above. The depolymerization steps and polymerization steps are completely independent and non-integrated.

Table 1 below reports the amounts of PTA and MEG monomers and of solid BHET monomer incorporated, the solid contents in the mixture of the feedstocks obtained at 110° C., the ratio of the number of diol units to the number of terephthalate units and the overall primary energy consumption for the production of 6.25 t/h of PET taking into account the incorporation of BHET resulting from the depolymerization process described above, for two ratios of diol units to terephthalate units (1.23 and 1.1). The results presented are calculated results, for different amounts of MEG introduced, 1 mol of BHET being regarded as replacing, in the mixture, 1 mol of PTA and 2 mol of MEG, and are based on process simulations incorporating solubility data and thermodynamic data locked to experimental points.

| | | Example 1a | Example 1b |
|---|---|---|---|
| Amount of PTA | [t/h] | 4.36 | 4.36 |
| Amount of MEG (fresh + recycled) for the polymerization | [t/h] | 1.65 | 1.39 |
| Amount of solid BHET incorporated | [t/h] | 1.74 | 1.74 |
| Diol units/terephthalate units ratio | [mol/mol] | 1.23 | 1.1 |
| Solids content | [vol %] | 49.2 | 51.5 |
| Primary energy consumption - Depolymerization step | [MMkcal/h] | 2.17 | 2.17 |
| Primary energy consumption - Polymerization step | [MMkcal/h] | 5.76 | 5.24 |
| Total primary energy consumption | [MMkcal/h] | 7.93 | 7.41 |

Example 2—According to the Invention

Production of PET Incorporating PET to be Recycled with Integration of the Depolymerization and Polymerization Processes 1.56 t/h of flakes resulting from a ground and washed feedstock of PET to be recycled, consisting of 50% by weight of opaque PET and 50% by weight of coloured PET, are melted in an extruder at 250° C. and mixed with 4.68 t/h of ethylene glycol (MEG). The mixture is then injected into a stirred reactor at 220° C. and at a pressure of 4 bara (i.e. 0.4 MPa). The residence time is set at 4 h. At the outlet of the reactor, the reaction effluent comprises 66% by weight of MEG, 27.4% by weight of BHET, 1.7% by weight of DEG, 0.2% by weight of water and 4.7% by weight of oligomers, pigments and other heavy compounds.

The ethylene glycol present in the reaction effluent is separated by evaporation in a sequence of 5 vessels operated at temperatures ranging from 200° C. to 124° C. and pressures from 0.1 MPa to 0.00025 MPa and is then sent to a stripping column and a rectification column.

At the end of this separation step, a stream rich in MEG (comprising 97% by weight of MEG) and a liquid stream rich in BHET of 1.76 t/h are recovered. The stream rich in MEG is fractionated: one portion is directly recycled to the depolymerization step and the monomer preparation step upstream of the esterification step, another portion is sent to a section for purification of the MEG (described below). The liquid stream rich in BHET comprises 87.1% by weight of BHET, 0.2% by weight of MEG, 0.1% by weight of DEG and 12.6% by weight of oligomers, pigments and other heavy compounds.

The liquid stream rich in BHET is subsequently injected into a short path distillation at a temperature of 205° C. and a pressure of 0.2 mbar (i.e. 0.00002 MPa). A prepurified BHET liquid effluent with a flow rate of 1.74 t/h is recovered by cooling the vapours in the short path distillation to 115° C. It comprises 99.8% by weight of BHET, 0.1% by weight of MEG and 0.1% by weight of DEG. A heavy residue with a flow rate of 0.27 t/h is also recovered at the outlet of the short path distillation: it comprises 93% by weight of oligomers, pigments and other heavy compounds and 7% by weight of BHET.

The prepurified BHET liquid stream is compressed up to 0.5 MPa and heated to 150° C. then feeds a fixed bed of activated carbon having an adsorption capacity equal to 5% of its weight. At the end of this step, a discoloured and depigmented BHET liquid stream is obtained, at a temperature of around 150° C. This discoloured and depigmented BHET liquid stream is directly sent to the monomer preparations step of the polymerization process.

The discoloured and depigmented BHET liquid stream is mixed in a mixing vessel at 110° C. and equipped with mechanical stirring, with:
- 4.36 t/h of terephthalic acid (PTA) and 1.65 t/h of monoethylene glycol (MEG) (Example 2a), or
- 4.36 t/h of terephthalic acid (PTA) and 1.39 t/h of monoethylene glycol (MEG) (Example 2b).

The mixture obtained in paste form is then sent to the esterification and polycondensation steps such as those described in Example 1.

The MEG-rich condensates from the polycondensation section are sent to the MEG purification section. The MEG purification section is similar to the one described in Example 1. The MEG recovered at the end of the MEG purification section has a purity of greater than 99.8%.

Table 2 below reports the amount of PTA and fresh MEG monomers and PET monomers to be recycled in order to produce 6.25 t/h of PET, the solids content obtained at the end of the step of preparing the monomer feedstocks, the ratio of the number of diol units to the number of terephthalate units in said step and the overall primary energy consumption for the integrated process. The results presented are calculated results, 1 mol of BHET being regarded as replacing, in the mixture, 1 mol of PTA and 2 mol of MEG, and are based on process simulations incorporating solubility data and thermodynamic data locked to experimental points.

|  |  | Example 2a | Example 2b |
|---|---|---|---|
| Amount of PTA | [t/h] | 4.36 | 4.36 |
| Amount of fresh MEG | [t/h] | 1.17 | 1.17 |
| Amount of rPET | [t/h] | 1.56 | 1.56 |
| Diol units/terephthalate units ratio in the monomer preparation step | [mol/mol] | 1.23 | 1.1 |
| Solids content in the monomer preparation step | [vol %] | 49.2 | 51.5 |
| Total primary energy consumption | [MMkcal/h] | 7.45 | 6.9 |

It clearly appears that at an equivalent ratio of number of diol units to number of terephthalatey units introduced into the step of preparing the polymerization feedstock (monomer preparation step), the overall process which integrates depolymerization steps and polymerization steps has a saving in energy consumption compared to the sum of the energy consumptions of a depolymerization process and of a polymerization process that are not integrated:
- for a diol units/terephthalate units ratio of 1.23:saving of 0.48 MMkcal/h (i.e. around 6%);
- for a diol units/terephthalate units ratio of 1.1:saving of 0.51 MMkcal/h (i.e. around 7%).

The invention claimed is:

1. A process for producing a terephthalate polyester from at least one feedstock of polyester to be recycled which comprises at least 10% by weight of opaque PET, comprising at least the following steps:
   a) a step of depolymerization of said feedstock of polyester to be recycled which comprises at least 10% by weight of opaque PET, comprising at least one reaction section fed with said feedstock of polyester to be recycled and a glycol feedstock which comprises at least one fraction of a purified diol stream, wherein said reaction section is operated, at a temperature between 150° C. and 400° C., at a pressure of at least 0.1 MPa, and at a residence time per reactor of 0.05 to and 10 h, in order to obtain a depolymerization reaction effluent,
   b) a separation step, comprising at least one separation section fed with said depolymerization reaction effluent obtained at the end of the depolymerization step a), in order to obtain at least one glycol effluent and one diester effluent,
   c) a step for purifying the diester effluent obtained at the end of step b), comprising at least one separation section that is fed with said diester effluent obtained at the end of step b) and operated at a temperature below or equal to 250° C., at a pressure less than or equal to 0.001 MPa, and at a liquid residence time per section of less than or equal to 10 min, then a discoloration section operated at a temperature of 100° C. to 250° C. and at a pressure of 0.1 to 1.0 MPa, in the presence of an adsorbent, in order to obtain a liquid purified diester effluent which comprises at least bis(2-hydroxyethyl) terephthalate BHET,
   d) a step for preparing a polymerization feedstock comprising at least one mixing section fed with at least one terephthalic feedstock which comprises terephthalic acid or dimethyl terephthalate, at least one fraction of said liquid purified diester effluent obtained in step c), and a diol monomer feedstock which is at least partly a fraction of a purified diol stream, wherein the amounts of at least said terephthalic feedstock and said fraction of the liquid purified diester effluent, introduced into said mixing section; is adjusted so that the ratio of the total number of moles of diol units of formula —[$C_{(n+1)}H_{(2n+2)}O_2$]—, n being an integer greater than or equal to 1, introduced into said mixing section, relative to the total number of moles of terephthalate units of formula —[CO—($C_6H_4$)—CO]—, introduced into said mixing section, is 1.0 to 2.0, wherein said mixing section is operated at a temperature of 100° C. to 150° C. and at a pressure greater than or equal to 0.1 MPa,
   e) a step for condensing said polymerization feedstock resulting from step d), in order to produce at least one condensation reaction effluent, one diol effluent and one aqueous effluent or one methanol effluent, wherein said condensation step comprises at least one reaction section operated at a temperature of 150° C. to 400° C., at a pressure of 0.05 to 1 MPa, and at a residence time of 0.5 to 10 h, and at least one separation section,
   f) a step of polycondensation of said condensation reaction effluent obtained in step e) in order to obtain at least said terephthalate polyester and a diol effluent, wherein said polycondensation step comprises at least one reaction section that comprises at least one reactor in which the polycondensation is carried out and that is operated at a temperature of 200° C. to 400° C., at a pressure of 0.0001 to 0.1 MPa, at a residence time of 0.1 to 5 h, said reaction section also comprising at least one drawing-off of said diol effluent, g) a step for treating the diols, comprising a recovery section fed at least by all or part of the glycol effluent resulting from step b) and all or part of the diol effluent resulting from step f), in order to obtain a diol stream to be treated, and a section for purification of said diol stream to be treated in order to obtain the purified diol stream which is sent, completely partly, to at least steps a) and d).

2. The production process according to claim 1, wherein said feedstock of polyester to be recycled comprises at least 15% by weight of opaque PET.

3. The production process according to claim 1, wherein said feedstock of polyester to be recycled comprises 0.1% and 10% by weight of pigments.

4. The production process according to claim 1, wherein the reaction section of step a) is fed with said feedstock of polyester to be recycled and with said glycol feedstock so that the amount of the glycol compound contained in said glycol feedstock corresponds, at the inlet of said reaction section, to 1 to 20 mol of glycol compound per mole of basic repeating unit of the polyester contained in said feedstock of polyester to be recycled.

5. The production process according to claim 1, wherein the separation section of step b) comprises a succession of 1 to 5 gas-liquid separations, carried out at a temperature of 100° C. to 250° C. and at a pressure of 0.00001 to 0.2 MPa.

6. The production process according to claim 1, wherein the separation section of the purification step c) uses a system of falling film or wiped film evaporation, by falling film or wiped film short path distillation, or by a succession of several falling film or wiped film short path distillations and/or evaporations, at a temperature below or equal to 250° C., and at a pressure less than or equal to 0.001 MPa.

7. The production process according to claim 1, wherein the adsorbent of the discoloration section of step c) is an activated carbon.

8. The production process according to claim 1, wherein the ratio of the total number of moles of diol units introduced into said mixing section, relative to the total number of moles of terephthalate units introduced into said mixing section, is 1.0 to 1.5.

9. The production process according to claim 4, wherein at the inlet of said reaction section, the amount of the glycol compound contained in the glycol feedstock corresponds to 3 to 10 mol of glycol compound per mole of basic repeating unit of the polyester contained in the feedstock of polyester to be recycled.

10. The production process according to claim 1, wherein the reaction section of step a) is operated at a temperature of 200° C. to 280° C.

11. The production process according to claim 1, wherein the reaction section of step a) is operated at a pressure of at least 0.4 MPa.

12. The production process according to claim 1, wherein the system of the separation section in the purification step c) is at a temperature below or equal to 200° C. and at a pressure of less than or equal to 0.0001 MPa.

13. The production process according to claim 1, wherein the ratio of the total number of moles of diol units introduced into said mixing section relative to the total number of moles of terephthalate units introduced into said mixing section is 1.0 to 1.3.

* * * * *